(12) United States Patent
Carter

(10) Patent No.: US 10,060,837 B2
(45) Date of Patent: Aug. 28, 2018

(54) DIFFERENTIAL PRESSURE CONSTANT VOLUME FLOW AIR SAMPLER

(75) Inventor: Michael S. Carter, Loveland, CO (US)

(73) Assignee: Western Energy Support and Technology, Inc, Loveland, CO (US)

( * ) Notice: Subject to any disclaimer, the term of this patent is extended or adjusted under 35 U.S.C. 154(b) by 332 days.

(21) Appl. No.: 13/092,096

(22) Filed: Apr. 21, 2011

(65) Prior Publication Data
US 2011/0259452 A1    Oct. 27, 2011

Related U.S. Application Data

(60) Provisional application No. 61/326,557, filed on Apr. 21, 2010, provisional application No. 61/346,657, filed on May 20, 2010.

(51) Int. Cl.
*G01N 1/22* (2006.01)
*G01N 1/24* (2006.01)

(52) U.S. Cl.
CPC ......... *G01N 1/2208* (2013.01); *G01N 1/2273* (2013.01); *G01N 1/2214* (2013.01); *G01N 2001/245* (2013.01); *Y10T 137/86002* (2015.04)

(58) Field of Classification Search
CPC ............... G01N 1/2208; G01N 1/2273; G01N 2001/245; G01N 1/2214
USPC .......................... 700/282; 73/864.71, 863.21
See application file for complete search history.

(56) References Cited

U.S. PATENT DOCUMENTS

| | | | | |
|---|---|---|---|---|
| 4,067,705 A | * | 1/1978 | Kurz | B01D 46/10 55/467 |
| 4,282,761 A | * | 8/1981 | Rosaen | G01F 1/22 73/861.58 |
| 4,686,848 A | * | 8/1987 | Casselberry et al. | 73/38 |
| 5,115,687 A | * | 5/1992 | Clingman et al. | 73/863.61 |
| 5,635,403 A | * | 6/1997 | Bailey | 436/66 |
| 6,514,721 B2 | * | 2/2003 | Spurrell | 435/30 |
| 6,867,413 B2 | * | 3/2005 | Basch | G01N 1/2208 250/255 |
| 7,667,839 B2 | * | 2/2010 | Bates | 356/337 |
| 8,188,874 B2 | * | 5/2012 | Calio | 340/606 |
| 2002/0112550 A1 | * | 8/2002 | Lawless | 73/863.21 |
| 2003/0070498 A1 | * | 4/2003 | Ohyama | G01N 35/1079 73/863.01 |
| 2003/0153844 A1 | * | 8/2003 | Smith | A61B 10/0051 600/573 |

(Continued)

FOREIGN PATENT DOCUMENTS

WO    WO 9306910 A1 *   4/1993

OTHER PUBLICATIONS

"Flow Measurement User Manual", Mar. 2005, Emerson Process Management, pp. 1-40.*

(Continued)

*Primary Examiner* — Jason Lin
(74) *Attorney, Agent, or Firm* — Russell Krajec; Krajec Patent Offices, LLC

(57) ABSTRACT

Disclosed is a differential pressure volume flow air sampler that measures temperature in a collection cavity, differential pressure between the measured ambient pressure and air pressure in a collection cavity. These parameters are used to calculate the volume air flow across a collection disk using a processor which adjusts a blower to maintain a substantially constant volume air flow through said air sampler from the surrounding atmosphere.

7 Claims, 2 Drawing Sheets

(56) References Cited

U.S. PATENT DOCUMENTS

| | | | | |
|---|---|---|---|---|
| 2003/0234366 A1* | 12/2003 | Basch | ............... | G01N 1/2208 |
| | | | | 250/393 |
| 2004/0125371 A1* | 7/2004 | Chang | ............... | G01J 3/4406 |
| | | | | 356/318 |
| 2004/0138079 A1* | 7/2004 | Becker et al. | ............. | 510/279 |
| 2005/0241417 A1* | 11/2005 | Kay | .......................... | 73/864.71 |
| 2006/0000296 A1* | 1/2006 | Salter | ..................... | B01L 9/06 |
| | | | | 73/863.01 |
| 2007/0229825 A1* | 10/2007 | Bates | ........................... | 356/339 |
| 2008/0087108 A1* | 4/2008 | Kreikebaum | ....... | G01N 1/2202 |
| | | | | 73/863.23 |

OTHER PUBLICATIONS

"MAS-100 Microbial Air Monitoring Systems", Sep. 2008, MERCK, pp. 1-12.*

* cited by examiner

DIFFERENTIAL PRESSURE CONSTANT VOLUME FLOW AIR SAMPLER

CROSS-REFERENCE TO RELATED APPLICATIONS

The present patent application is based upon and claims the benefit of U.S. Provisional Patent Application Ser. No. 61/326,557, filed on Apr. 21, 2010, by Michael S. Carter, entitled "Differential Pressure Constant Volume Flow Air Sampler," and U.S. Provisional Patent Application Ser. No. 61/346,657, filed on May 20, 2010, by Michael S. Carter, entitled "Differential Pressure Constant Volume Flow Air Sampler," which applications are hereby specifically incorporated herein by reference for all that they disclose and teach.

BACKGROUND OF THE INVENTION

Air samplers are used for various purposes in various environments. For example, air samplers may be used by pharmaceutical companies to test the air in clean rooms to monitor airborne microbes.

SUMMARY

An embodiment of the present invention may therefore comprise a differential pressure volume flow air sampler that regulates the volume flow of air through a microbial air monitoring system comprising: a housing having a collection cavity and an exhaust cavity; a head having a head flow coefficient, the head being removably attached to the housing so that the head can be interchangeably used with the housing; a temperature probe disposed in the collection cavity that generates a temperature signal that indicates air temperature in the collection cavity; a differential pressure sensor that measures a differential pressure, which is a difference in pressure between ambient air pressure and collection cavity air pressure, and generates a differential pressure signal; a blower that regulates the volume air flow through the microbial air monitoring system in response to the control signal; a processor that calculates volume air flow through the volume flow air sampler and generates a control signal using the temperature signal, the ambient pressure signal and the differential pressure signal using the following equation:

$$Q\text{dot}=C^*[dP^*T/Pa]^{0.5}$$

where Qdot=the volume air flow in liters per minute; dP=the differential pressure in kilopascals [kPa]; Pa=the ambient air pressure in kilopascals [kPa]; T=the air temperature in Kelvins [K]; and C=the head flow coefficient in liters per minute/$\sqrt{T}$ in Kelvins.

An embodiment of the present invention may further comprise a method of maintaining a substantially constant volume air flow through an air flow sampler comprising: moving air through a head and a housing using an adjustable blower; detecting air temperature of the air; generating an air temperature signal indicative of air temperature; applying the air temperature signal to a processor; detecting ambient air pressure and air pressure in the collection chamber to obtain a differential air pressure between the ambient air pressure and the air pressure in the collection chamber; generating a differential pressure signal from the differential air pressure; applying the ambient air pressure signal and the differential air pressure signal to the processor; obtaining head flow coefficient data indicative of a flow coefficient of the head; calculating the volume air flow through the air flow sampler in a processor using the equation:

$$Q\text{dot}=C^*[dP^*T/Pa]^{0.5}$$

where: Qdot=the volume air flow; dP=the differential air pressure; Pa=the ambient air pressure; T=the air temperature; and C=the flow coefficient of the head; generating a control signal from the processor to control the adjustable blower to maintain the substantially constant volume air flow through the air flow sampler.

An embodiment of the present invention may further comprise a system for maintaining a substantially constant volume air flow through an air flow sampler comprising: means for moving air through a head and a housing using an adjustable blower; means for detecting air temperature of the air; means for generating an air temperature signal indicative of the air temperature; means for detecting ambient air pressure and air pressure in the collection chamber to obtain a differential air pressure signal indicative of a difference between the ambient air pressure and the air pressure in the collection chamber; means for calculating the volume air flow through the air flow sampler in a processor using the equation:

$$Q\text{dot}=C^*[dP^*T/Pa]^{0.5}$$

where: Qdot=the volume air flow; dP=the differential air pressure; Pa=the ambient air pressure; T=the air temperature; and C=a flow coefficient of the head; means for controlling the adjustable blower to maintain said substantially constant volume air flow through said air flow sampler.

DETAILED DESCRIPTION OF THE EMBODIMENTS

Figure 1:
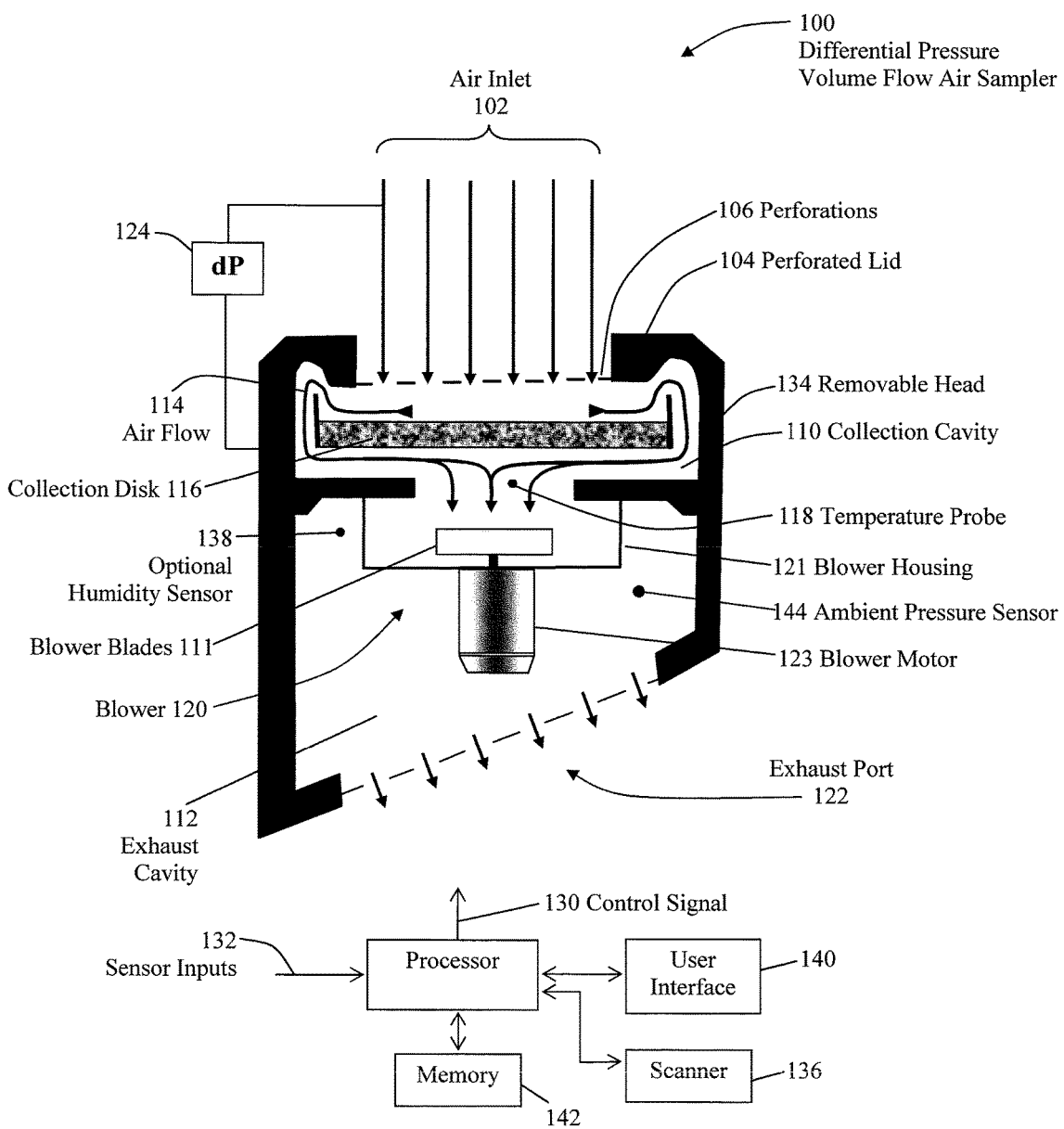
FIG. 1 is a schematic cross-sectional view of one embodiment of a differential pressure constant volume flow air sampler.

FIG. 1 is a cross-sectional view of one embodiment of a differential pressure constant volume flow air sampler 100. As illustrated in FIG. 1, the volume flow air sampler 100 includes a perforated lid 104 having perforations 106, which constitute air inlet 102. Air is drawn through the air inlet 102 in response to blower 120 that pulls air through the collection cavity 110 and discharges into the exhaust cavity 112. Air from the air inlet 102 flows through the perforations 106 and impacts collection disk 116. The perforated lid 104 forms part of a removable head 134 that can be easily replaced each time a new air sample is taken. Collection disk 116 may comprise, for example, a petri dish that is coated with a biological medium. The blower 120 causes an air flow 114, so that air from air inlet 102 flows across and impacts the biological medium on the collection disk 116. The air flowing through the air inlet 102, via perforations 106, impacts the top surface of the collection disk 116 on which the biological medium is located. The air flow 114 then proceeds around the outside of the collection disk 116 in the collection cavity 110. Air is then drawn into the blower housing 121 of blower 120, as a result of blower blades 111 being driven by the blower motor 123. The air from the blower 120 is then pushed into the exhaust cavity 112 and exhausted through exhaust port 122. A reduced pressure is created in the collection cavity 110, as a result of the blower 120. This causes air to flow through the air inlet 102, from the surrounding environment, which is at ambient pressure, to the lower pressure created by the blower 120 in the collection cavity 110.

The differential pressure sensor 124, illustrated in FIG. 1, measures the difference between the air pressure in the collection cavity versus the ambient air pressure at the air inlet 120. For each air sample, the removable head 134 may be replaced with a new head. In addition, collection disk 116 is also replaced. Each of the removable heads 134 may have an identifying code, such as a bar code, magnetic code, or other code known to those skilled in the art, which identifies the removable head 134, as well as the unique flow coefficients for that head. Each of the removable heads 134 is calibrated during the manufacturing process and encoded with the calibration data, indicating the flow coefficient for each removable head. Processor 128 retrieves the calibration data from memory 142 after obtaining the identification data from scanner 136. Various types of heads can be used with the differential pressure volume flow air sampler 100. Each of these different heads may have different flow coefficients. The flow coefficient for the head, as well as the collection disk 113 that is placed in the head, is determined or calculated in advance. The removable head 134 is then encoded with identifying information that links the removable head 134 to the proper flow coefficient for that head. Scanner 136 is used to scan the encoding on the removable head 134, so that processor 128 can retrieve the flow coefficient information for that particular removable head 134. The head flow coefficient includes the flow coefficient for the head 134, which includes the perforations 106 in perforated lid 104. The flow coefficient retrieved by processor 128 from storage is then utilized in Equation 1 to calculate volume air flow. Alternative, the removable head 134 can be encoded with the flow coefficient data directly. In this manner, the scanner 136 can read the flow coefficient data for the removable head 134 and provided it to the processor 128, so that the flow coefficient data does not have to be stored in memory 142 and retrieved by processor 128 from memory 142.

The perforated lid 104, illustrated in FIG. 1, may have a different number of perforations or perforations that are not the same size as perforations in other perforated lids. The differential pressure sensor 124 is able to determine the pressure drop across the perforations 106 and very accurately account for differences in pressure between the ambient pressure of the surrounding atmosphere and the pressure within the collection cavity 110.

Once the volume air flow (Qdot) is calculated in accordance with Equation 1 below, adjustments can then be made to the blower 120 by the processor 128, via control signal 130, to allow the interchangeable use of perforated lids 104, while maintaining a substantially constant volume air flow through differential pressure volume flow air sampler 100. As also illustrated in FIG. 1, temperature probe 118 measures the ambient temperature of the air in the collection cavity 112 at the inlet to the blower 120. This information is used by processor 126 to determine the volume flow of air through the perforations 106 that impinges upon the collection disk 116. Processor 126 calculates the volume air flow from the following equation:

$$Q\text{dot} = C^*[dP^*T/Pa]^{0.5} \tag{1}$$

where:
Qdot=volume air flow in liters per minute;
dP=differential pressure in kilopascals [kPa];
Pa=ambient pressure in kilopascals [kPa];
T=air temperature in Kelvin [K]; and,
C=head flow coefficient in liters per minute/$\sqrt{T}$ in Kelvins.

By using Equation (1) to calculate airflow volume, a highly precise determination can be made of the actual volume air flow across the collection disk 116. Equation (1) accounts for differences in the density of the air due to temperature and ambient pressure changes. For example, a different volume flow would occur across the collection plate for a constant airflow if the airflow monitor is located at sea level at 70° versus being located at approximately 5,000 feet in Denver, Colo., at 80°. Further, changes in barometric and temperature readings from day to day will change the volume flow readings. Processor 128 receives the sensor inputs 132, which include the collection cavity temperature signal, the differential pressure signal and the ambient pressure signal to calculate the volume air flow through the differential pressure volume flow air sampler 100. A feedback control signal 130 is then generated, which is applied to the blower to control the speed of the blower 120.

As further shown in FIG. 1, an optional humidity sensor 138 can be used to generate a humidity signal that is applied to processor 128 as a sensor input 132. The humidity signal indicates the humidity level of the ambient air. In biological chambers, the humidity is fixed at a constant level by the air handling system of the biological chamber. Biological chambers may be used for making pharmaceuticals or other medications. The differential pressure volume flow air sampler 100 can also be used in other environments, such as in processing plants and other areas where the humidity level is not strictly controller and, as such, the air density changes. There are at least three major factors that affect air density. The first is elevation (ambient pressure), the second is temperature, and the third is humidity. In applications were humidity is not controlled, the optional humidity sensor 138 can provide humidity data to the processor 128, so that processor 128 can control blower 120, by way of control signal 130. User interface 140 allows a user to monitor and adjust the operation of the differential pressure volume flow air sampler 100.

Figure 2:
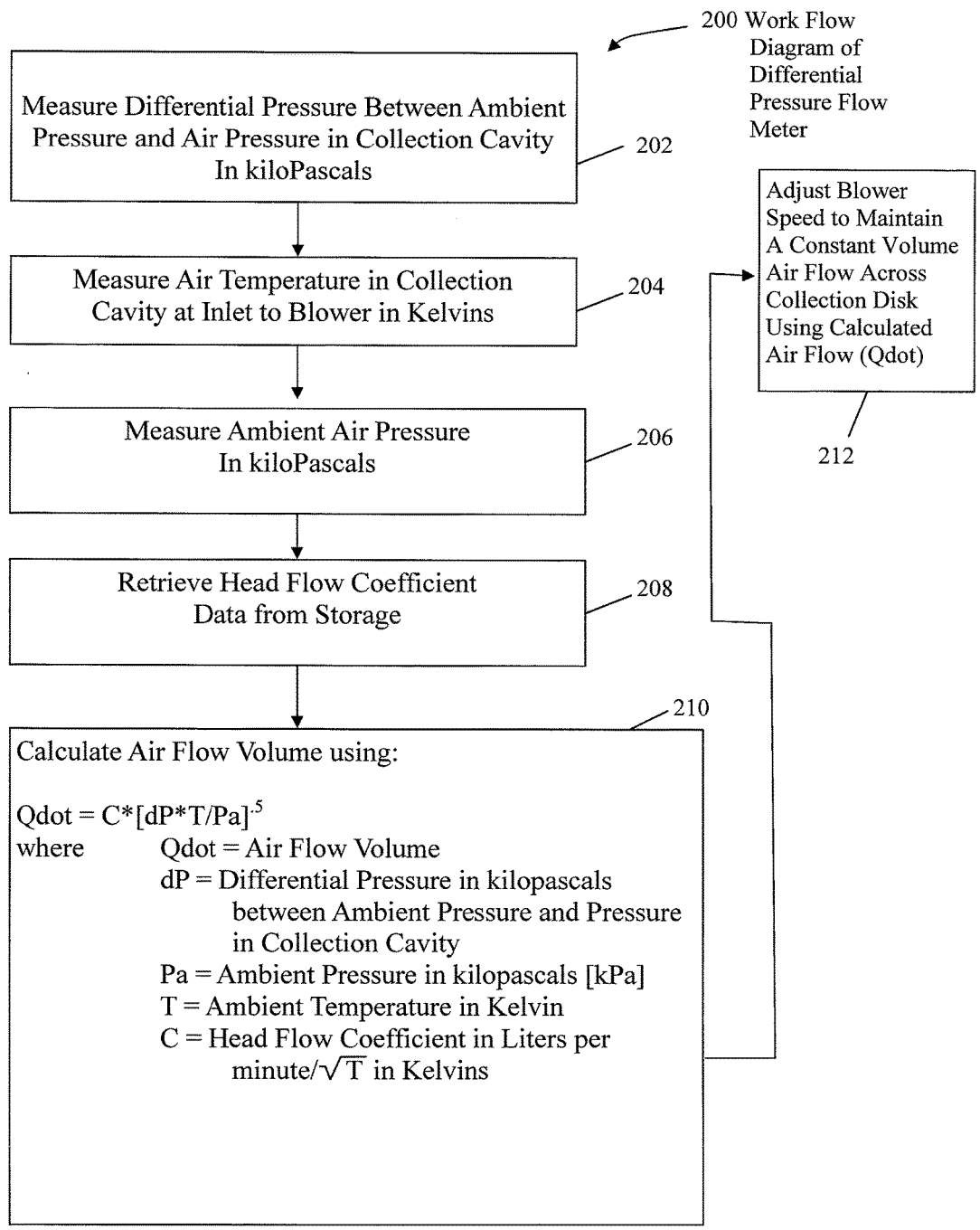
FIG. 2 is a work flow diagram in accordance with one embodiment of the present invention.

FIG. 2 is a work flow diagram 200 of the volume flow air sampler 100, illustrated in FIG. 1. As illustrated in FIG. 2, at step 202, the differential pressure volume flow air sampler 100 measures differential pressure between the inlet, which is at ambient pressure, and the collection cavity. A differential pressure signal is generated by the differential pressure sensor 124 and applied to processor 128, as one of the sensor inputs 132. Differential pressure sensor 124 may also generate an ambient pressure signal that comprises one of the sensor inputs 132, that are sent to processor 128. At step 204, the ambient air temperature is measured of the air in the collection cavity at the inlet of blower 120. A collection cavity air temperature signal is generated and applied to processor 128 as one of the sensor inputs 132. At step 206, the ambient pressure is measured using sensor 144 and applied to processor 128 as one of the sensor inputs 132. At step 208, the head flow coefficient is obtained from memory 142. As indicated above, the head flow coefficient is generated using a calibration process that is performed during the manufacture of the removable head 134. The head flow coefficient data is stored in memory 142 via user interface 140. Upon reading the encoded information from the removable head 134, using scanner 136, the processor retrieves the head coefficient data from memory 142. At step 210, the volume air flow is calculated in processor 126, using Equation (1). At step 212, the processor generates a control signal 130 that adjusts the blower speed to maintain a constant volume flow across the collection disk 116 using the calculated volume air flow (Qdot).

Hence, a differential pressure volume flow air sampler 100 provides information regarding volume flow that can be used to adjust the operational speed of a blower in a microbial air monitoring system. The differential pressure volume flow air sampler adjusts for changes in pressure and temperature to provide a highly accurate system for maintaining a constant volume flow rate across a collection disk 116.

The foregoing description of the invention has been presented for purposes of illustration and description. It is not intended to be exhaustive or to limit the invention to the precise form disclosed, and other modifications and variations may be possible in light of the above teachings. The embodiment was chosen and described in order to best explain the principles of the invention and its practical application to thereby enable others skilled in the art to best utilize the invention in various embodiments and various modifications as are suited to the particular use contemplated. It is intended that the appended claims be construed to include other alternative embodiments of the invention except insofar as limited by the prior art.

What is claimed is:

1. An air flow sampler comprising:
   a housing;
   a perforated lid having a first side and a second side, said first side being exposed to ambient air, said perforated lid comprising a plurality of holes:
   a collection cavity disposed on said second side of said perforated lid;
   a removable head comprising said perforated lid and said collection cavity, said removable head having a flow coefficient, said flow coefficient is generated using a calibration process that is performed during manufacturing of the removable head and said flow coefficient being electronically retrievable;
   a blower downstream from said collection cavity capable of causing air to flow from said first side of said perforated lid to said second side of said perforated lid;
   a differential pressure sensor capable of measuring a differential pressure across said perforated lid by measuring ambient air pressure on said first side of said perforated lid and a second pressure on said second side of said perforated lid and upstream from said blower, said differential pressure sensor configured to generate a differential pressure signal; and
   a processor configured to: receive a differential pressure signal from said differential pressure sensor; receive said flow coefficient by reading a bar code of the removable head; and determine a flow rate based on said differential pressure signal and said flow coefficient; wherein the blower is controlled by the processor based on the flow rate.

2. The airflow sampler of claim 1 further comprising:
   a humidity sensor configured to generate a humidity signal; said processor further configured to receive said humidity signal and determine said flow rate based on said differential pressure signal, said flow coefficient and said humidity signal.

3. The airflow sampler of claim 2, said processor further configured to:
   operate said blower to achieve a predetermined volume of air flow per unit time.

4. The air flow sampler of claim 3 further comprising:
   a removable collection disk mounted in said collection cavity.

5. The air flow sampler of claim 4, said collection disk comprising a biological medium.

6. The air flow sampler of claim 1, said removable head having said flow coefficient embedded thereon.

7. The air flow sampler of claim 1 further comprising:
   a second removable head having a second flow coefficient.

* * * * *